United States Patent [19]

Sakurai et al.

[11] 4,098,705

[45] Jul. 4, 1978

[54] SULFUR CONTAINING MOLYBDENUM DIHYDROCARBYLDITHIOCARBAMATE COMPOUND

[75] Inventors: Toshio Sakurai, Yokohama; Akio Nishihara, Tokyo; Takuro Handa, Tokyo; Hidekatsu Katoh, Tokyo; Yoshiro Tomoda, Tokyo; Kazumi Aoki, Tokyo; Makoto Yoto, Tokyo, all of Japan

[73] Assignee: Asahi Denka Kogyo K.K., Tokyo, Japan

[21] Appl. No.: 709,856

[22] Filed: Jul. 29, 1976

[30] Foreign Application Priority Data

Aug. 7, 1975 [JP] Japan ............................... 50-96135
Aug. 7, 1975 [JP] Japan ............................... 50-96136
Mar. 3, 1976 [JP] Japan ............................... 51-22749

[51] Int. Cl.$^2$ .................. C10M 1/54; C10M 3/48; C10M 5/28; C07F 11/00
[52] U.S. Cl. .............................. 252/33.6; 260/429 R; 260/429 K
[58] Field of Search ................ 260/429 R, 429 K; 252/33.6

[56] References Cited

U.S. PATENT DOCUMENTS 3,419,589  12/1968  Larson ............................ 260/429
3,509,051  4/1970  Farmer et al. ................... 252/33.6

*Primary Examiner*—Delbert E. Gantz
*Assistant Examiner*—J. Thierstein
*Attorney, Agent, or Firm*—Blanchard, Flynn, Thiel, Boutell & Tanis

[57] ABSTRACT

A compound having the following general formula (I);

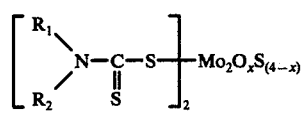

wherein $R_1$ and $R_2$ stand for a hydrocarbyl group having from 1 to 24 carbon atoms, $x$ is a number of 0.5 – 2.3, useful as an additive for lubricants.

17 Claims, No Drawings

SULFUR CONTAINING MOLYBDENUM DIHYDROCARBYLDITHIOCARBAMATE COMPOUND

BACKGROUND OF THE INVENTION

1. Field of the Invention

This invention relates to a sulfur containing molybdenum dihydrocarbyldithiocarbamate compound which is useful as an additive for lubricants.

Furthermore, this invention relates to a method producing such compound, and to a lubricating composition containing such compound.

2. Description of the Prior Art

In the field of this invention some prior arts are known. One of them is the description of Japanese Pat. Publication No. 24562/1970 and almost the same description as that is found in Japanese Pat. Publication No. 6362/1974 (those correspond to U.S. Pat. No. 3,356,702). Those Publications teach a method of producing the compound having the general formula $[R_2N-CS_2]_2-Mo_2O_mS_{(4-m)}$ wherein R is a hydrocarbyl group and m is a number of 2.35 – 3, which compound is useful as an additive for lubricants. But that compound has insufficient lubricating properties, insufficient properties under extreme pressure conditions and insufficient anti-oxidation properties. The compound according to this invention cannot be obtained by the method described in those Publications.

Japanese Pat. Laid-Open Application (not examined) No. 56202/1973 teaches a compound having the general formula $[R_2N-CS_2]_2-Mo_2S_4$ wherein R is an alkyl group, which compound is useful as an additive for lubricants. But that compound has a corrosive action on copper-containing materials, so the use of that compound has been limited.

Other descriptions mentioned as prior art to this invention are set forth in H. Isoyama and T. Sakurai, TRIBOLOGY international August 1974, 151–160, T.Sakurai, H. Okabe and H. Isoyama, Bulletin of The Japan Petroleum Institute 13(2) November 1971, 243–249, and T. Sakurai and H. Isoyama, ibid 16(2) November 1974, 112–117. The compounds used in those descriptions are the same compounds as used in the above mentioned Japanese Patent Publications.

SUMMARY OF THE INVENTION

It is an object of this invention to provide a compound useful as an additive for lubricants, and further having improved lubricating properties, higher extreme pressure properties, higher anti-oxidation properties and less corrosive action on copper-containing materials and other materials. It is another object of this invention to provide a method of producing the compound with reliability. It is another object of this invention to provide a lubricant having many improved properties and less corrosive action.

The compound of this invention has the following general formula;

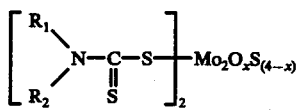 (I)

wherein $R_1$ and $R_2$ stand for a hydrocarbyl group having from 1 to 24 carbon atoms, which may be substituted by hydroxy group, and $R_1$ and $R_2$ may be the same or different; x is a number from 0.5 to 2.3, preferably 0.75 to 2.1. One of the practically preferable groups for $R_1$ and $R_2$ in the general formula (I) is an alkyl group having from 1 to 24 carbon atoms, more preferably having from 2 to 18 carbon atoms, such as n-butyl, isobutyl, tert-butyl group, n-octyl group, 2-ethylhexyl group, n-nonyl group, n-decyl group, lauryl group, stearyl group, methyl group, ethyl group, n-propyl, isopropyl group, n-valeryl, isovaleryl group, amyl group, 1,1,3,3-tetramethylbutyl group, n-heptyl and iso-heptyl group. Another of the practically preferable groups for $R_1$ and $R_2$ in the general formula (I) is an alicyclic hydrocarbyl group, which may be substituted by an alkyl group, such as cyclohexyl group and 2-methyl cyclohexyl group. Yet another practically preferable groups for $R_1$ and $R_2$ in the general formula (I) is an aromatic hydrocarbyl group such as benzyl group, 4-methyl benzyl group, 3-methoxybenzyl group, 3,4-dimethoxybenzyl group and 4-ethoxyphenyl group. Still another practically preferable groups for $R_1$ and $R_2$ in the general formula (I) is a hydroxyalkyl group such as hydroxy ethyl group.

The solubility of the compound of this invention in oil, fat, grease and artificial lubricating oils such as polyethers and polyesters, can be controlled by the kind of $R_1$ and $R_2$ of the general formula (I). According to this invention, for example, a compound which is very soluble in mineral oil is obtained by the use of 2-ethylhexyl group, stearyl, benzyl group, iso-valeryl or tert-octyl group.

On the contrary, a compound which is almost insoluble in mineral oil is obtained by use of, for example, n-butyl or cyclohexyl group.

The compound having the general formula (I) is obtained, with reliability, by reaction between carbon disulfide and a secondary amine having the following general formula;

 (II)

wherein $R_1$ and $R_2$ have the same meanings as defined in the general formula (I),
under a temperature of higher than 80° C, in water medium containing a molybdenum compound selected from the group consisting of molybdenum trioxide, alkaline metal molybdates, ammonium molybdate and their mixtures, and containing a sulfide compound selected from the group consisting of an alkaline metal hydrogensulfide, ammonium hydrogensulfide, an alkaline metal sulfide, ammonium sulfide and their mixtures, in the molar ratio of molybdenum compound to sulfide compound in the range between 1 : 0.05 and 1 : 4, having a pH of 0.5 – 10.

For the purpose of more reliable production, simpler operation of the reaction and quality control, the molybdenum compound is at least partially, preferably almost completely, reacted with the sulfide compound before addition of carbon disulfide and the secondary amine, to the reaction system. The reaction easily takes place with agitation under a temperature of 10° – 60° C for 30 – 60 minutes. In the case of using molybdenum trioxide, it is preferable to use the powdered one in order to react faster with the sulfide compound, which will increase its solubility in water. Practically preferable alkaline metal molybdates are sodium molybdate and potassium molybdate. Also, the solution or suspension produced by reaction between molybdenum trioxide and an aqueous alkaline metal hydroxide solution can be used in this invention. Practically preferable alkaline metal hydrogensulfides and alkaline metal sulfides are sodium hydrogensulfide, sodium sulfide, potassium hydrogensulfide and potassium sulfide. And an aqueous solution of the sulfide compound is more preferable than the solid, in view of the reactivity, the simple operation and economy. Also, the solution produced by reaction between an aqueous alkaline metal hydroxide solution and hydrogen sulfide, is used in this invention, and furthermore, the aqueous alkaline metal hydroxide solution may contain these molybdenum compounds.

The molar ratio of the molybdenum compound to the sulfide compound is an important factor in order to determine the number of '$x$' in the general formula (I). The molar ratio of the sulfide compound to the molybdenum compound is from 0.05 to 4, preferably from 0.08 to 3.8.

The pH of an aqueous solution or suspension containing a molybdenum compound and a sulfide compound, to be maintained before addition of carbon disulfide and a secondary amine, is also an important factor to determine the number of '$x$' in the general formula (I) and further influences the yield of the product. The higher the pH, the smaller is the number of '$x$'. The pH is from 0.5 to 10, preferably from 1 to 8, more preferably from 1.2 to 7.5. In case the pH is greater than 10 or smaller than 0.5, the yield of the product remarkably decreases. The aqueous solution or suspension dissolving or suspending a molybdenum and a sulfide compound have generally a pH value higher than 10, by this is easily controlled by adding an acid, especially a mineral acid such as hydrochloric acid and sulfuric acid.

A preferred secondary amine having general formula (II) is a dialkylamine such as di-n-butylamine, di-n-octylamine, dilaurylamine, distearylamine, diisobutylamine, di-2-ethylhexylamine, dimethylamine, diethylamine, di-n-propylamine, diisopropylamine, diheptylamine, diisoheptylamine, and diamylamine.

A preferred secondary amine having general formula (II) further includes a dialicyclic amine such as dicyclohexylamine and di-2-methylcyclohexylamine, a diaromatic such as dibenzylamine, di-4-methylbenzylamine, di-3-methoxybenzylamine and di-3,4-dimethoxybenzylamine, and dialkanolamines such as diethanolamine.

The secondary amine having general formula (II) further includes unsymmetrical secondary amine having alkyl, alicylic and/or aromatic groups, such as methyl-n-butylamine, ethyllaurylamine, ethylstearylamine, isopropyl-n-octylamine, n- or iso-butyl-2-ethylhexylamine, cyclohexyl-n-butylamine, cyclohexyl-2-ethylhexylamine, cyclohexyl-benzylamine, stearylbenzylamine, 2-ethylhexylbenzylamine, 2-ethylhexylvalerylamine, butylbenzylamine, laurylbenzylamine, ethyl-2-ethylhexylamine, i-valeryl-2-ethylhexylamine, N-2-ethylhexyl-3,4-dimethoxybenzylamine, N-1,1,3,3-tetramethylbutyl-N-2-ethylhexylamine, 2-ethylhexylbutylamine, 2-ethylhexyllaurylamine, 2-ethylhexylstearylamine and i-valerylbenzylamine.

The molar ratios of the molybdenum compounds, secondary amine and carbon disulfide are not limited. But an excessive amount of the reactants is not preferable from an industrial and economical viewpoint, and practically preferable molar ratios of molybdenum compounds: secondary amine: carbon disulfide are 1 : 1 - 2 : 1 - 2, more preferably 1 : 1 - 1.4 : 1 - 1.4. The temperature of the reaction of secondary amine, carbon disulfide and the molybdenum compounds is higher than 80° C, generally 80° - 105° C, and practically preferably 90° - 100° C. The reaction time is about 2 - 10 hours. The pressure during the reaction may be depressed and may be compressed. The obtained reaction products are generally colored solids, but they are easily refined by filtering, washing by water and organic solvents and recrystallization from organic solvents. Benzene, methanol, butanol and chloroform are used as an organic solvent for refining.

According to this invention, lubricants are provided, containing the compound having general formula (I) which has advantages such as improved lubricating properties, higher extreme pressure properties, higher anti-oxidation properties, no corrosive action and other good properties. The lubricants of this invention contain, as essential components, base material and 0.05 - 30 weight %, preferably 0.2 - 10 weight % of the compound having general formula (I). The base materials are lubricating oil, grease, fat and other artificial material such as mineral oil (turbine oil, gear oil, light oil, heavy oil, etc.) animal oil (tallow, lard oil, etc.), vegetable oil (rape seed oil, palm oil, castor oil, etc.), artificial oil (mono- or poly-ester, polyether, silicon oil, etc.), etc. The lubricants may contain some other ingredients. Examples of such ingredients are thickeners (lithium soap, other soaps, clay and other fillers, etc.), rust preventatives, corrosion inhibitor, antioxidant, and pour point depressants. The contents of such ingredients are known, and are for example, 0.1 - 10 weight %.

It is an effect of this invention to provide a compound useful as an additive for lubricants. Further, it is an effect of this invention to provide a compound having higher lubricating properties, higher extreme pressure properties, higher anti-oxidation properties and less corrosive properties against copper containing materials and other materials.

It is another effect of this invention to provide a method to produce the compound, constantly.

It is another effect fo this invention to provide a lubricants having many higher properties and less corrosive properties.

The invention is further described in the following illustrative examples, which are not limiting.

In the below-mentioned Examples, sodium molybdate dihydrate was used as sodium molybdate.

EXAMPLE 1

Into a reactor were added 100 ml of water, 0.05 mole of sodium sulfide nonahydrate and 0.05 mole of sodium molybdate. The pH of the mixture was adjusted to 2.8 by adding 20% sulfuric acid while agitating the mixture. Into the mixture were added 0.1 mole of di-n-butylamine and 0.1 mole of carbon disulfide, and the mixture was agitated for 30 minutes at room temperature and then was reacted for 4 hours at 95° - 102° C. Then, the precipitate was filtered and washed by methanol and dried. 16.8 g of fulvescent solid having a melting point of 271° - 272° C, was obtained. The yield is 95.5%. The results of elementary analysis are as follows: C = 31.5%, H = 4.7%, N = 4.2%, S = 29.4%, Mo = 28.4%. The number of '$x$' in general formula (I) was determined as 1.55.

EXAMPLE 2

Into a reactor were added 100 ml of water, 0.05 mole of sodium sulfide nonahydrate and 0.05 mole of sodium molybdate. The pH of the mixture was adjusted to 2.8 by adding 20% sulfuric acid while agitating the mixture. Into the mixture were added 0.075 mole of di-n-butylamine and 0.075 mole of carbon disulfide, and the mixture was agitated for 30 minutes at room temperature and then was reacted for 4 hours at 95° – 102° C. Then, the precipitate was filtered and washed by methanol and dried. Fulvescent solid having a melting point of 270° – 271° C was obtained. The yield is 92.8%. The results of elementary analysis are as follows: S = 29.5%. The number of 'x' in general formula (I) was determined as being 1.50.

EXAMPLE 3

Into a reactor were added 100 ml of water, 0.05 mole of sodium sulfide nonahydrate and 0.05 mole of sodium molybdate. The pH of the mixture was adjusted to 2.8 by adding 20% sulfuric acid while agitating the mixture. Into the mixture were added 0.055 mole of di-n-butylamine and 0.075 mole of carbon disulfide, and the mixture was agitated for 30 minutes at room temperature and then was reacted for 4 hours at 95° – 102° C. Then, the precipitate was filtered and washed by methanol and dried. Yellowish orange solid having a melting point of 269° – 270° C was obtained. The yield is 96.3%. The results of elementary analysis are as follows: S = 30.6%. The number of 'x' in general formula (I) was determined as being 1.35.

EXAMPLE 4

Into a reactor were added 100 ml of water, 0.06 mole of sodium sulfide nonahydrate and 0.05 mole of sodium molybdate. The pH of the mixture was adjusted to 7.1 by adding 20% sulfuric acid while agitating the mixture. Into the mixture were added 0.1 mole of di-n-butylamine and 0.1 mole of carbon disulfide, and the mixture was agitated for 30 minutes at room temperature and then was reacted for 4 hours at 95° – 102° C. Then, the precipitate was filtered and washed by methanol and dried. Yellowish orange solid having a melting point of 271° – 273° C was obtained. The yield is 94.8%. The results of elementary analysis are as follows: S = 29.4%. The number of 'x' in general formula (I) was determined as being 1.55.

EXAMPLE 5

Into a reactor were added 100 ml of water, 0.15 mole of sodium sulfide nonahydrate and 0.05 mole of sodium molybdate. The pH of the mixture was adjusted to 7.1 by adding 20% sulfuric acid while agitating the mixture. Into the mixture, were added 0.1 mole of di-n-butylamine and 0.1 mole of carbon disulfide, and the mixture was agitated for 30 minutes at room temperature and then was reacted for 4 hours at 95° – 102° C. Then, the precipitate was filtered and washed by methanol and dried. Yellowish orange solid having a melting point of 215° – 217° C was obtained. The yield is 83.0%. The results of elementary analysis are as follows: S = 32.5%, Mo = 28.4%. The number of 'x' in general formula (I) was determined as being 0.75.

EXAMPLE 6

Into a reactor were added 100 ml of water, 0.05 mole of aqueous sodium hydrogen sulfide and 0.05 mole of sodium molybdate. The pH of the mixture was adjusted to 2.8 by adding 20% sulfuric acid while agitating the mixture. Into the mixture were added 0.1 mole of di-n-butylamine and 0.1 mole of carbon disulfide, and the mixture was agitated for 30 minutes at room temperature and then was reacted for 4 hours at 95° – 102° C. Then, the precipitate was filtered and washed by methanol and dried. Fulvescent solid having a melting point of 271° – 272° C., was obtained. The yield is 95.0%. The results of elementary analysis are as follows: S = 29.4%. The number of 'x' in general formula (I) was determined as being 1.55.

EXAMPLE 7

Into a reactor were added 100 ml of water, 0.05 mole of sodium sulfide nonahydrate and 0.05 mole of sodium molybdate. The pH of the mixture was adjusted to 1.6 by adding 20% sulfuric acid while agitating the mixture. Into the mixture were added 0.1 mole of di-n-butylamine and 0.1 mole of carbon disulfide, and the mixture was agitated for 30 minutes at room temperature and then was reacted for 4 hours at 95° – 102° C. Then, the precipitate was filtered and washed by methanol and dried. Yellow solid having a melting point of 270° – 271° C was obtained. The yield is 94.8%. The results of elementary analysis are as follows: S = 27.1%. The number of 'x' in general formula (I) was determined as being 2.1.

EXAMPLE 8

Into a reactor were added 100 ml of water, 0.05 mole of potassium sulfide nonahydrate and 0.05 mole of sodium molybdate. The pH of the mixture was adjusted to 2.8 by adding 20% sulfuric acid while agitating the mixture. Into the mixture, were added 0.1 mole of dilaurylamine and 0.1 mole of carbon disulfide, and the mixture was agitated for 30 minutes at room temperature and then was reacted for 4 hours at 95° – 102° C. Then, the precipitate was filtered and washed by methanol and dried. Pale yellow solid having a melting point of 172° – 173° C was obtained. The yield is 93.2%. The results of elementary analysis are as follows: S = 18.0%. The number of 'x' in general formula (I) was determined as being 1.70.

EXAMPLE 9

Into a reactor were added 100 ml of water, 0.05 mole of potassium sulfide nonahydrate and 0.05 mole of sodium molybdate. The pH of the mixture was adjusted to 2.8 by adding 20% sulfuric acid while agitating the mixture. Into the mixture were added 0.1 mole of dicyclohexylamine and 0.1 mole of carbon disulfide, and the mixture was agitated for 30 minutes at room temperature and then was reacted for 4 hours at 95° – 102° C. Then, the precipitate was filtered and washed by methanol and dried. Pale yellow solid having a melting point of 290° – 291° C, was obtained. The yield is 90.0%. The number of 'x' in general formula (I) calculated from the results of elementary analysis was determined as being 1.63.

EXAMPLE 10

Into a reactor were added 100 ml of water, 0.05 mole of sodium sulfide nonahydrate and 0.05 mole of sodium molybdate. The pH of the mixture was adjusted to 2.8 by adding 20% sulfuric acid while agitating the mixture. Into the mixture were added 0.055 mole of stearylbenzylamine and 0.055 mole of carbon disulfide, and the mixture was agitated for 30 minutes at room temperature and then was reacted for 4 hours at 95° – 102° C. Then, the precipitate was filtered and washed by methanol and dried. Yellow solid having a melting point of 90° – 91.5° C was obtained. The yield is 95.0%. The number of 'x' in general formula (I) calculated from the results of elementary analysis was determined as being 1.67.

EXAMPLE 11

Into a 200 ml flask equipped with an agitator, a thermometer, gas inlet tube and tap funnel were added 100 ml of water, 0.07 mole of sodium hydroxide and 0.05 mole of sodium molybdate. 0.065 mole of hydrogen sulfide was introduced into the mixture while agitating at room temperature. The pH of the mixture was adjusted to 2.8 by adding 20% sulfuric acid while agitating the mixture. Into the mixture were added 0.075 mole of di-n-butylamine and 0.075 mole of carbon disulfide, and the mixture were agitated for 30 minutes at room temperature and then was reacted for 4 hours at 95° – 102° C. Then, the precipitate was filtered and washed by methanol and dried. Yellowish orange solid having a melting point of 269° – 270° C was obtained. The yield is 93.7%. The number of 'x' in general formula (I) calculated from the results of elementary analysis was determined as being 1.27.

EXAMPLE 12

Into a reactor were added 100 ml of water 0.05 mole of ammonium sulfide nonahydrate and 0.05 mole of ammonium molybdate. The pH of the mixture was adjusted to 2.8 by adding 20% sulfuric acid while agitating the mixture. Into the mixture were added 0.1 mole of di-n-butylamine and 0.1 mole of carbon disulfide, and the mixture was agitated for 30 minutes at room temperature and then was reacted for 4 hours at 95° – 102° C. Then, the precipitate was filtered and washed by methanol and dried. The same product was obtained as Example 1.

EXAMPLE 13

Into a reactor were added 100 ml of water 0.05 mole of sodium sulfide nonahydrate and 0.05 mole of sodium molybdate. The pH of the mixture was adjusted to 2.8 by adding 20% sulfuric acid while agitating the mixture. Into the mixture were added 0.075 mole of diethylamine and 0.075 mole of carbon disulfide, and the mixture was agitated for 30 minutes at room temperature and then was reacted for 4 hours at 95° – 102° C. Then, the precipitate was filtered and washed by methanol and dried. Fulvescent solid having a melting point of 289° – 291° C was obtained. The yield is 91.8%. The number of 'x' in general formula (I) calculated from the results of elementary analysis was determined as being 1.53.

EXAMPLE 14

Into an air-tight reactor were added 300 ml of water and 1.0 mole of powdered molybdenum trioxide. Then, 1.25 mole of sodium hydrogen sulfide (38 wt.% aqueous solution) were added under agitation and reacted for 30 minutes. The pH of the mixture was adjusted to 1.9 by adding 30 wt.% hydrochloric acid while agitating the mixture. Into the mixture were added 1.1 mole of di-n-butylamine and 1.1 mole of carbon disulfide, and the mixture was agitated for 30 minutes at room temperature and was reacted for 4 hours at 95° – 102° C. Then, the precipitate was filtered and washed by benzene and methanol and dried. 16.8 g of fulvescent solid having a melting point of 271° – 272° C was obtained. The yield is 95.0%. The results of elementary analysis are as follows: C = 31.5%, H = 4.8%, N = 4.2%, S = 29.5%, Mo = 28.4%. The number of 'x' in general formula (I) was determined as being 1.52.

EXAMPLE 15

Into an air-tight reactor were added 300 ml of water and 1.0 mole of powdered molybdenum trioxide. Then 3.6 mole of sodium hydrogen sulfide (38 wt.% aqueous solution) were added under agitation and reacted for 30 minutes. The pH of the mixture was adjusted to 2.8 by adding 25% sulfuric acid while agitating the mixture. Into the mixture were added 1.2 mole of di-n-butylamine and 1.2 mole of carbon disulfide, and the mixture was agitated for 30 minutes at room temperature and then was reacted for 4 hours at 95° – 102° C. Then, the precipitate was filtered and washed by methanol and dried. Yellowish orange solid having a melting point of 214° – 215° C was obtained. The yield is 88.0%. The results of elementary analysis are as follows: S = 32.8%. The number of 'x' in general formula (I) was determined as being 0.85.

EXAMPLE 16

Into an air-tight reactor were added 300 ml of water and 1.0 mole of powdered molybdenum trioxide. Then 1.2 mole of sodium hydrogen sulfide (36 wt.% aqueous solution) were added under agitation and reacted for 30 minutes. The pH of the mixture was adjusted to 2.6 by adding 30 wt.% hydrochloric acid while agitating the mixture. Into the mixture were added 1.1 mole of dilaurylamine and 1.1 mole of carbon disulfide, and the mixture was agitated for 30 minutes at room temperature and then was reacted for 4 hours at 95° – 102° C. Then, the precipitate was filtered and washed by methanol and dried. Pale yellow solid having a melting point of 172° – 173° C was obtained. The yield is 90.8%. The results of elementary analysis are as follows: S = 18.1%. The number of 'x' in general formula (I) was determined as being 1.68.

EXAMPLE 17

0.05 mole of powdered molybdenum trioxide, 0.06 mole of sodium hydrogen sulfide (38 wt.% aqueous solution), 0.055 mole of di-2-ethylhexylamine and 0.055 mole of carbon disulfide were reacted under the same conditions as Example 15 (the pH was adjusted to 2.5 with 30 wt.% hydrochloric acid). The oily reaction product was separated and poured into organic solvents such as benzene, alcohols, chloroform and their mixtures, and then the obtained powdery product was filtered and dried. A slightly yellow solid having a melting point of 89° – 89.5° C was obtained. The yield was 40%. The number of 'x' in general formula (I) was determined as being 1.97.

EXAMPLE 18

0.05 mole of powdered molybdenum trioxide, 0.055 mole of sodium hydrogen sulfide (38 wt.% aqueous solution), 0.0505 mole of 2-ethylhexylbenzylamine and 0.0505 mole of carbon disulfide were reacted under the same conditions as Example 15 (the pH was adjusted 2.0 with 30 wt.% hydrochloric acid). The reaction product was filtered and washed by organic solvents such as benzene, alcohols and their mixture, and then dried. A slightly yellow solid having a melting point of 60° – 63°

C was obtained. The yield was 85%. The number of 'x' in general formula (I) was determined as being 1.97.

EXAMPLE 19

0.05 mole of powdered molybdenum trioxide, 0.055 mole of sodium hydrogen sulfide (38 wt.% aqueous solution), 0.055 mole of ethyl-2-ethylhexylamine and 0.055 mole of carbon disulfide were reacted under the same conditions as Example 15 (the pH was adjusted to 2.5 with 30 wt.% hydrochloric acid). The reaction product was filtered and washed by organic solvents such as benzene, alcohols and their mixture, and then dried. A dark brown solid having a decomposition temperature of 239° – 240° C was obtained. The yield was 87%. The number of 'x' in the general formula (I) was determined as being 1.93.

EXAMPLE 20

0.05 mole of powdered molybdenum trioxide, 0.055 mole of sodium hydrogen sulfide (38 wt.% aqueous solution), 0.055 mole of n-butyl-2-ethylhexylamine and 0.055 mole of carbon disulfide were reacted under the same conditions as Example 15 (the pH was adjusted to 2.8 with 30 wt.% hydrochloric acid). The oily reaction product was separated and poured into organic solvents such as benzene, alcohols, chloroform and their mixture, and then the obtained powdery product was filtered and dried. A brown solid having a melting point of 239° – 241° C was obtained. The yield was 85%. The number of 'x' in the general formula (I) was determined as being 1.95.

EXAMPLE 21

0.05 mole of powdered molybdenum trioxide, 0.06 mole of sodium hydrogen sulfide (38 wt.% aqueous solution), 0.055 mole of i-valeryl-2-ethylhexylamine and 0.055 mole of carbon disulfide were reacted under the same conditions as Example 15 (the pH was adjusted to 2.8 with 35 wt. % hydrochloric acid). The oily reaction product was separated and poured into organic solvents such as benzene, alcohols, chloroform and their mixture, and then the obtained powdery product was filtered and dried. A red brown solid having a melting point of 128° – 130.5° C was obtained. The yield was 80%. The number of 'x' in the general formula (I) was determined as being 1.90.

EXAMPLE 22

0.05 mole of powdered molybdenum trioxide, 0.055 mole of sodium hydrogen sulfide (38 wt.% aqueous solution), 0.055 mole of 2-ethylhexyllaurylamine and 0.055 mole of carbon disulfide were reacted under the same conditions as Example 15 (the pH was adjusted to 2.5 with 30 wt.% hydrochloric acid). The reaction product was filtered and washed by organic solvents such as benzene, alcohols and their mixture, and then dried. An orange color solid having a melting point of 69° – 72° C was obtained. The yield was 90%. The number of 'x' in the general formula (I) was determined as being 1.95.

EXAMPLE 23

0.05 mole of powdered molybdenum trioxide, 0.06 mole of sodium hydrogen sulfide (38 wt.% aqueous solution), 0.055 mole of cyclohexyl-2-ethylhexylamine and 0.055 mole of carbon disulfide were reacted under the same conditions as Example 15 (the pH was adjusted to 3.5 with 30 wt.% hydrochloric acid). The oily reaction product was separated and poured into organic solvents such as benzene, alcohols, chloroform and their mixture, and then the obtained powdery product was filtered and dried. A red brown solid having a melting point of 135° – 138° C was obtained. The yield was 85%. The number of 'x' in the general formula (I) was determined as being 1.90.

EXAMPLE 24

0.05 mole of powdered molybdenum trioxide, 0.055 mole of sodium hydrogen sulfide (38 wt.% aqueous solution), 0.055 mole of di-ethanolamine and 0.055 mole of carbon disulfide were reacted under the same conditions as Example 15 (the pH was adjusted to 2.8 with 35 wt.% hydrochloric acid). The oily reaction product was separated and poured into organic solvents such as benzene, alcohols, chloroform and their mixture, and then the obtained powdery product was filtered and dried. A brown solid having a melting point of 215° – 220° C was obtained. The yield was 80%. The number of 'x' in the general formula (I) was determined as being 1.90.

EXAMPLE 25

0.05 mole of powdered molybdenum trioxide, 0.055 mole of sodium hydrogen sulfide (38 wt.% aqueous solution), 0.055 mole of N-2-ethylhexyl-3,4-dimethoxybenzylamine and 0.055 mole of carbon disulfide were reacted under the same conditions as Example 15 (the pH was adjusted to 3.75 with 30 wt.% hydrochloric acid). The oily reaction product was separated and poured into organic solvents such as benzene, alcohols, chloroform and their mixture, and then the obtained powdery product was filtered and dried. A brown solid having a melting point of 160° – 163° C was obtained. The yield was 80%. The number of 'x' in the general formula (I) was determined as being 1.90.

EXAMPLE 26

0.05 mole of powdered molybdenum trioxide, 0.07 mole of sodium hydrogen sulfide (38 wt.% aqueous solution), 0.055 mole of distearylamine and 0.055 mole of carbon disulfide were reacted under the same conditions as Example 15 (the pH was adjusted with 30 wt.% hydrochloric acid). The reaction product was filtered and washed by organic solvents such as benzene, alcohols and their mixture, and then dried. A brown solid having a melting point of 162° – 165° C was obtained. The yield was 90%. The number of 'x' in the general formula (I) was determined as being 1.95.

EXAMPLE 27

0.05 mole of powdered molybdenum trioxide, 0.07 mole of sodium hydrogen sulfide (38 wt.% aqueous solution), 0.055 mole of di-n-amylamine and 0.055 mole of carbon disulfide were reacted under the same conditions as Example 15 (the pH was adjusted to 3.75 with 35 wt.% hydrochloric acid). The reaction product was filtered and washed by organic solvents such as benzene, alcohols and their mixture, and then dried. An orange color solid having a melting point of 239° – 240° C was obtained. The yield was 89%. The number of 'x' in the general formula (I) was determined as being 1.90.

EXAMPLE 28

0.05 mole of powdered molybdenum trioxide, 0.07 mole of sodium hydrogen sulfide (38 wt.% aqueous solution), 0.055 mole of N-1,1,3,3-tetramethylbutyl-N- ethylhexylamine and 0.055 mole of carbon disulfide were reacted under the same conditions as Example 15 (the pH was adjusted to 3.75 with 35 wt.% hydrochloric acid). The oily reaction product was separated and washed with organic solvents such as benzene, alcohols and their mixture, and then the oily product was separated and solvents were evaporated and dried. A brown oil was obtained. The yield was 85%. The number of '$x$' in the general formula (I) was determined as being 1.95.

COMPARATIVE PRODUCTION EXAMPLE 1.

0.1 mole of sodium molybdate dihydrate is dissolved in 100 ml of water, and neutralized with sulfuric acid. 0.2 mole of dibutylamine and 0.2 mole of carbon disulfide are added to the neutralized mixture and agitated for 30 minutes. Then the mixture is refluxed for 5.5 hours at 97° – 100° C. Then the reaction mixture is filtered and washed with toluene. 23.8 g of yellowish solid having a melting point of 259° C is obtained. The results of elementary analysis are as follows: C = 31.5% H = 5.28% N = 4.1% S = 25.1% Mo = 28.0% And the number of '$x$' in general formula (I) was determined as 2.5.
And the reaction product refluxed for 8 hours is the same product as the above solid product.

EXAMPLES 29–34 AND COMPARATIVE EXAMPLES 1–3

The compounds obtained in the above Examples are used in an amount of 1 weight % in a solution or suspension of turbine oil. The diameters of the wear tracks created by the tests of the Shell four ball machine at 80 Kg of load and 1800 r.p.m. are measured. The results are shown in Table 1.

Table 1

| Ex. No. | Compound | value of '$x$' in the general formula (I) | The diameters of the wear tracks (mm) |
|---|---|---|---|
| 29 | the product of Example 1 | 1.55 | 0.64 |
| 30 | the product of Example 3 | 1.35 | 0.64 |
| 31 | the product of Example 5 | 0.75 | 0.63 |
| 32 | the product of Example 8 | 1.70 | 0.40 |
| 33 | the product of Example 9 | 1.63 | 0.43 |
| 34 | the product of Example 10 | 1.67 | 0.38 |
| Comparative Example 1 | Molybdenum disulfide | — | 1.13 |
| 2 | $\left(\begin{array}{c}\text{n-C}_4\text{H}_9\\ \phantom{x}\\ \text{n-C}_4\text{H}_9\end{array}\right\!\!\!\text{N}\!-\!\text{CS}_2\!\!-\!\!\!\left.\phantom{x}\right)_{\!2}\!\!\text{Mo}_2\text{S}_4$ | 0 | 0.63 |
| 3 | blank | — | 2.41 |

EXAMPLES 35–40 AND COMPARATIVE EXAMPLES 4 and 5

The compounds obtained the above Examples are mixed with Lithium-12-hydroxystearate grease at the ratio of 0.005 mole per 100 g of the grease. The welding loads measured by the tests of the Shell four ball machine are shown in Table 2.

Table 2

| Ex. No. | Compounds | Welding load (Kg) |
|---|---|---|
| 35 | the product of Example 1 | 320 |
| 36 | the product of Example 3 | 350 |
| 37 | the product of Example 5 | 380 |
| 38 | the product of Example 8 | 330 |
| 39 | the product of Example 9 | 320 |
| 40 | the product of Example 10 | 360 |
| Comparative Ex. 4 | Molybdenum disulfide | 250 |
| 5 | blank | 160 |

EXAMPLES 41–46 AND COMPARATIVE EXAMPLES 6 and 7

1 weight % of the compounds obtained in the above Examples are mixed with Lithium grease. The degree of dropping of the pressure by the tests of Norma Hoffman bomb oxidation test after 100 hours at 98.9° C, are shown in Table 3.

Table 3

| Ex. No. | Compound | The degree of dropping the pressure (Kg/cm$^2$) |
|---|---|---|
| 41 | the product of Example 1 | 0.26 |
| 42 | the product of Example 3 | 0.23 |
| 43 | the product of Example 5 | 0.21 |
| 44 | the product of Example 8 | 0.23 |
| 45 | the product of Example 9 | 0.23 |
| 46 | the product of Example 10 | 0.23 |
| Comparative Ex. 6 | the product of Comparative production Example | 0.37 |
| 7 | blank | 0.65 |

EXAMPLES 47–50 AND COMPARATIVE EXAMPLE 8

3 parts of the compounds obtained in the above Examples are mixed with 100 parts of dioctylsebacate and 0.01 parts of zinc dibutyldithiocarbamate. This mixture is dropped on polished copper plates at 100° C for 24 hours, and then the surface conditions of the copper plates are observed. The results of the observation and an appraised values according to ASTM Copper Strip Tarnish Test D-130, are shown in Table 4.

Table 4

| Ex. No. | Compound | Surface Conditions | Appraised value |
|---|---|---|---|
| 47 | the product of Example 1 | No cloudy, No corrosion | 1a |
| 48 | the product of Example 3 | No cloudy, No corrosion | 1a |
| 49 | the product of Example 9 | A little cloudy, No corrosion | 1a |
| 50 | the product of Example 10 | No cloudy, No corrosion | 1a |

Table 4-continued

| Ex. No. | Compound | Surface Conditions | Appraised value |
|---|---|---|---|
| Comparative Example 8 | 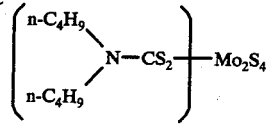 | found brown or dark gray corrosion | 4b |

EXAMPLES 51–63 AND COMPARATIVE EXAMPLES 9–11

The compounds obtained in the above Examples are used as 1 wt.% solution or suspension in spindle oil, and their effects on the load-carrying capacity in Falex Test (ASTM D-3233-73) are determined.

| Ex. No. | Used Compound | Load-carrying capacity (lb) |
|---|---|---|
| 51 | the product of Example 17 | 1,750 |
| 52 | the product of Example 18 | 1,250 |
| 53 | the product of Example 19 | 1,000 |
| 54 | the product of Example 20 | 1,750 |
| 55 | the product of Example 21 | 1,750 |
| 56 | the product of Example 22 | 1,500 |
| 57 | the product of Example 23 | 1,250 |
| 58 | the product of Example 24 | 1,750 |
| 59 | the product of Example 25 | 1,250 |
| 60 | the product of Example 26 | 1,000 |
| 61 | the product of Example 27 | 1,250 |
| 62 | the product of Example 28 | 1,250 |
| 63 | the product of Example 29 and 2% of tricresylphosphate | 2,500 |
| Comparative Ex. | | |
| 9 | 3% of molybdenum disulfide | 750 |
| 10 | 2% of tricresylphosphate | 750 |
| 11 | blank | 750 |

EXAMPLE 66, AND COMPARATIVE EXAMPLE 12 and 13

3 weight % of the compounds obtained in the above Examples are mixed with Lithium grease. The Last Non-Seizure Load (L.N.S.L.) and Load Wear Index (L.W.I.) are examined by Shell-4-ball E.P. Tester and the results are shown in Table 6.

Table 6

| Ex. No. | Used compounds | L.N.S.L. | L.W.I. |
|---|---|---|---|
| 66 | the product of Example 1 | 126 Kg. | 56 |
| Comparative Ex. No. | | | |
| 12 | the product of Comparative Example 1 | 80 Kg. | 48 |
| 13 | blank | 50 Kg. | 30 |

What we claim is:

1. A composition having the formula:

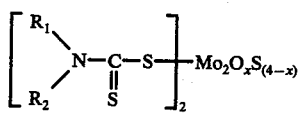

wherein $R_1$ and $R_2$, which are the same or different, are selected from the group consisting of hydrocarbyl having from one to 24 carbon atoms and hydroxy-substituted hydrocarbyl having from one to 24 carbon atoms, and $x$ is a number of from 0.75 to 2.1.

2. A composition having the formula

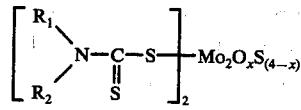

wherein $R_1$ and $R_2$, which are the same or different, are selected from the group consisting of alkyl having 2 to 18 carbon atoms, cyclohexyl, 2-methylcyclohexyl, benzyl, 4-methylbenzyl, 3-methoxybenzyl, 3,4-dimethoxybenzyl, 4-ethoxyphenyl and hydroxyethyl, and $x$ is a number of from 0.75 to 2.1.

3. A composition as claimed in claim 2, in which $R_1$ and $R_2$ both are n-butyl.

4. A method for preparing a composition having the formula

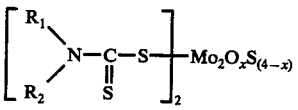

wherein $R_1$ and $R_2$, which are the same or different, are selected from the group consisting of hydrocarbyl having from one to 24 carbon atoms and hydroxy-substituted hydrocarbyl having from one to 24 carbon atoms, and $x$ is a number of from 0.75 to 2.1, which comprises adding (a) carbon disulfide and (b) a secondary amine having the formula $\begin{smallmatrix}R_1\\R_2\end{smallmatrix}>NH$, wherein $R_1$ and $R_2$ have the same meaning as set forth above, to (c) a reaction mixture consisting essentially of water, a molybdenum compound selected from the group consisting of molybdenum trioxide, alkaline metal molybdates, ammonium molybdate and mixtures thereof, and a sulfide compound selected from the group consisting of alkaline metal hydrogensulfides, ammonium hydrogensulfide, alkaline metal sulfides, ammonium sulfide and mixtures thereof, wherein the molar ratio of said molybdenum compound/sulfide compound is from 1/1.05 to ¼, said reaction mixture having a pH of 0.5 to 10, reacting the mixture of (a), (b) and (c) at a temperature of higher than 80° C to form a composition of the first mentioned formula and recovering said composition from the reaction mixture.

5. A method according to claim 4 in which the reaction mixture (c) of water, said molybdenum compound and said sulfide compound is maintained at from 10° to 60° C, for from 30 to 60 minutes, prior to adding (a) and (b) thereto, to react said molybdenum compound with said sulfide compound.

6. A method according to claim 5 in which said alkaline metal molybdate is sodium molybdate or potassium molybdate, said alkaline metal hydrogensulfide is sodium hydrogensulfide or potassium hydrogensulfide and said alkaline metal sulfide is sodium sulfide or potassium sulfide.

7. A method according to claim 5 in which the molybdenum compound is obtained by reaction between molybdenum trioxide and an aqueous alkaline metal hydroxide solution.

8. A method according to claim 5 in which the sulfide compound is obtained by reaction between sulfide and an aqueous alkaline metal hydroxide solution.

9. A method according to claim 5 in which the molar ratio of said molybdenum compound/sulfide compound is from 1/0.08 to 1/3.8.

10. A method according to claim 9 in which the pH of (c) is from 1 to 8.

11. A method according to claim 9 in which the pH of (c) is from 1.2 to 7.5.

12. A method according to claim 10 in which the molar ratio of molybdenum compound:secondary amine-carbon disulfide is 1:1 to 2:1 to 2.

13. A method according to claim 10 in which the molar ratio of molybdenum compound:secondary amine:carbon disulfide is 1:1 to 1.4:1 to 1.4.

14. A method according to claim 12 in which the reaction temperature is from 80° to 105° C and the reaction time is from 2 to 10 hours.

15. A method according to claim 12 in which the reaction temperature is from 90° to 100° C and the reaction time is from 2 to 10 hours.

16. A lubricating composition containing from 0.05 to 30 percent by weight of a composition as claimed in claim 11 and the balance is a conventional lubricant material.

17. A lubricating composition containing from 0.2 to 10 percent by weight of a composition as claimed in claim 11 and the blance is a conventional lubricant material.

* * * * *

UNITED STATES PATENT AND TRADEMARK OFFICE
CERTIFICATE OF CORRECTION

PATENT NO. : 4 098 705
DATED : July 4, 1978
INVENTOR(S) : Toshio Sakurai et al

It is certified that error appears in the above-identified patent and that said Letters Patent are hereby corrected as shown below:

Column 14, line 53; change "1/1.05" to --- $\frac{1}{0.05}$ ---.

Column 15, line 11; after "between" insert ---hydrogen---.

Column 16, line 3; change "amine-carbon" to ---amine:carbon---.

Column 16, line 15; change "ll" to ---1---.

Column 16, line 19; change "ll" to ---1---.

change "blance" to ---balance---.

Signed and Sealed this

Nineteenth Day of December 1978

[SEAL]

Attest:

RUTH C. MASON
*Attesting Officer*

DONALD W. BANNER
*Commissioner of Patents and Trademarks*